United States Patent [19]

North

[11] 4,306,557

[45] Dec. 22, 1981

[54] VACUUM UROLOGICAL SURGICAL IRRIGATING SOLUTION COLLECTING SYSTEM

[76] Inventor: Daniel A. North, 312 Crestline Dr., Missoula, Mont. 59801

[21] Appl. No.: 937,874

[22] Filed: Aug. 29, 1978

[51] Int. Cl.³ .............................................. A61M 1/00
[52] U.S. Cl. .................................. 128/276; 137/205; 141/59
[58] Field of Search .................. 128/7, 213 R, 214 F, 128/224, 227–228, 240, 248, 275, 276, 277, 278, 294, 295; 137/205; 141/59

[56] References Cited

U.S. PATENT DOCUMENTS

| | | | |
|---|---|---|---|
| 2,597,715 | 5/1952 | Erikson | 128/272 |
| 3,529,599 | 9/1970 | Folkman | 128/275 |
| 3,680,560 | 8/1972 | Pannier, Jr. et al. | 128/276 |
| 3,685,517 | 8/1972 | Reynolds et al. | 128/277 |
| 3,704,709 | 12/1972 | Sorenson et al. | 128/277 |
| 3,719,197 | 3/1973 | Pannier, Jr. et al. | 128/276 |
| 3,773,211 | 11/1973 | Bridgman | 128/276 |
| 3,845,765 | 11/1974 | Ikeda | 128/277 |
| 3,848,628 | 11/1974 | Deaton et al. | 128/276 |
| 3,861,396 | 1/1975 | Vaillancourt et al. | 128/350 R |
| 3,874,367 | 4/1975 | Ayres | 128/276 |
| 3,908,660 | 9/1975 | Kaplan et al. | 128/350 R |
| 3,946,735 | 3/1976 | De Wall | 128/278 |
| 3,982,546 | 9/1976 | Friend | 128/350 R |
| 3,998,227 | 12/1976 | Holbrook et al. | 128/276 |
| 4,111,204 | 9/1978 | Hessel | 128/276 |

Primary Examiner—C. Fred Rosenbaum
Attorney, Agent, or Firm—Browdy and Neimark

[57] ABSTRACT

A vacuum urological surgical irrigating solution-collecting system of the continuous flow type employs a flexible thin-walled disposable collecting receptacle in a rigid outer supporting container, with spacers to hold the collecting receptacle away from the outer container and to establish a space therebetween. A higher vacuum is maintained between the collecting receptacle and the rigid container walls than is inside the collecting receptacle. A fine-adjustment vacuum regulator is employed to maintain the required balanced urological relative pressure conditions between the inside and the outside of the vacuum collecting receptacle to maintain said receptacle in a fully expanded condition. The spacers consist of perforated half-cylindrical rigid strips arranged vertically with their side edges secured to the inside surface of the rigid container wall and with their rounded faces directed inwardly. A circular bottom spacer is provided between the bottom of the collecting receptacle and the bottom of the outer container, and a top spacer disc assembly is provided between the top of the collecting receptacle and the rigid container top cover.

16 Claims, 9 Drawing Figures

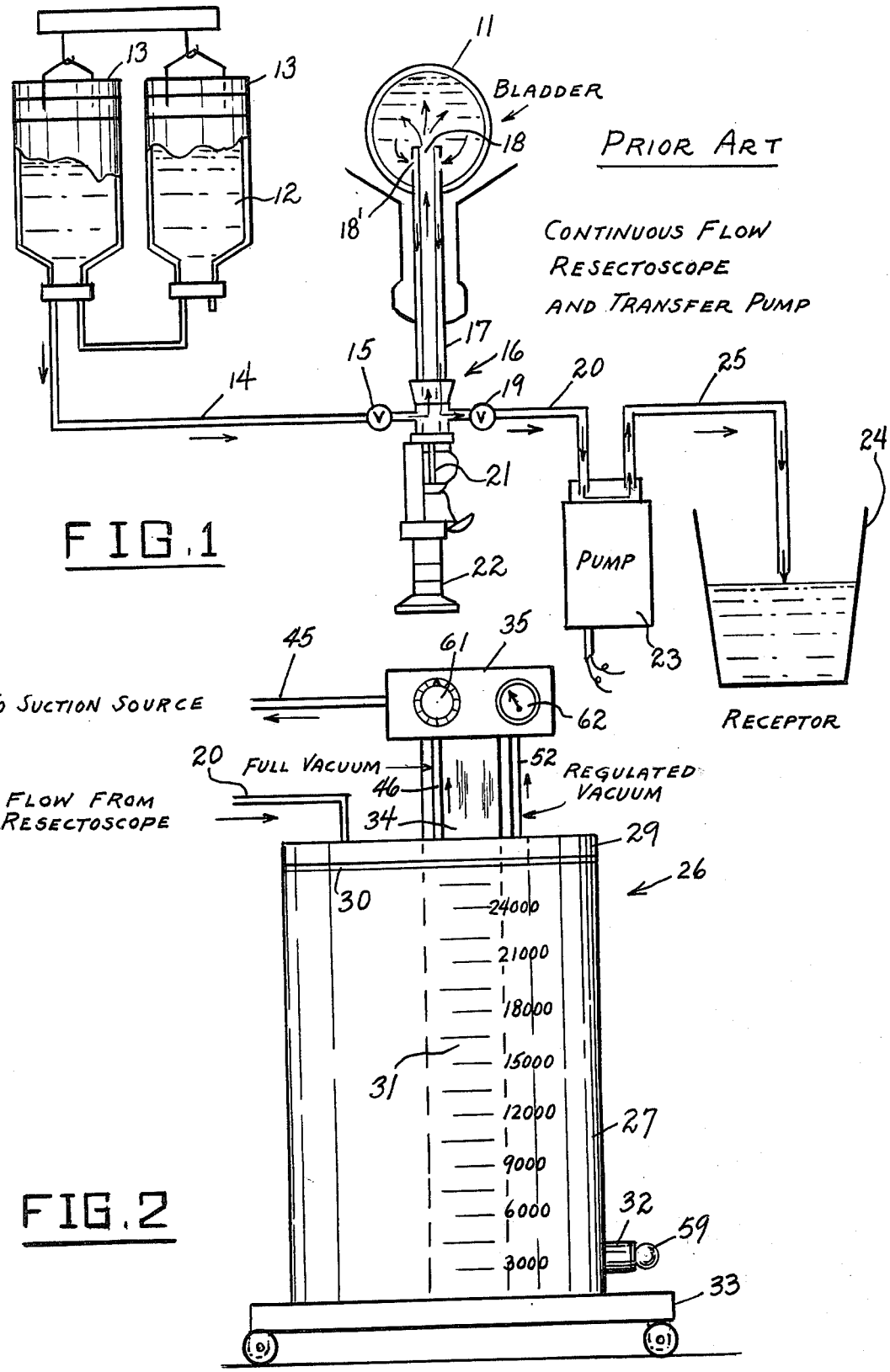

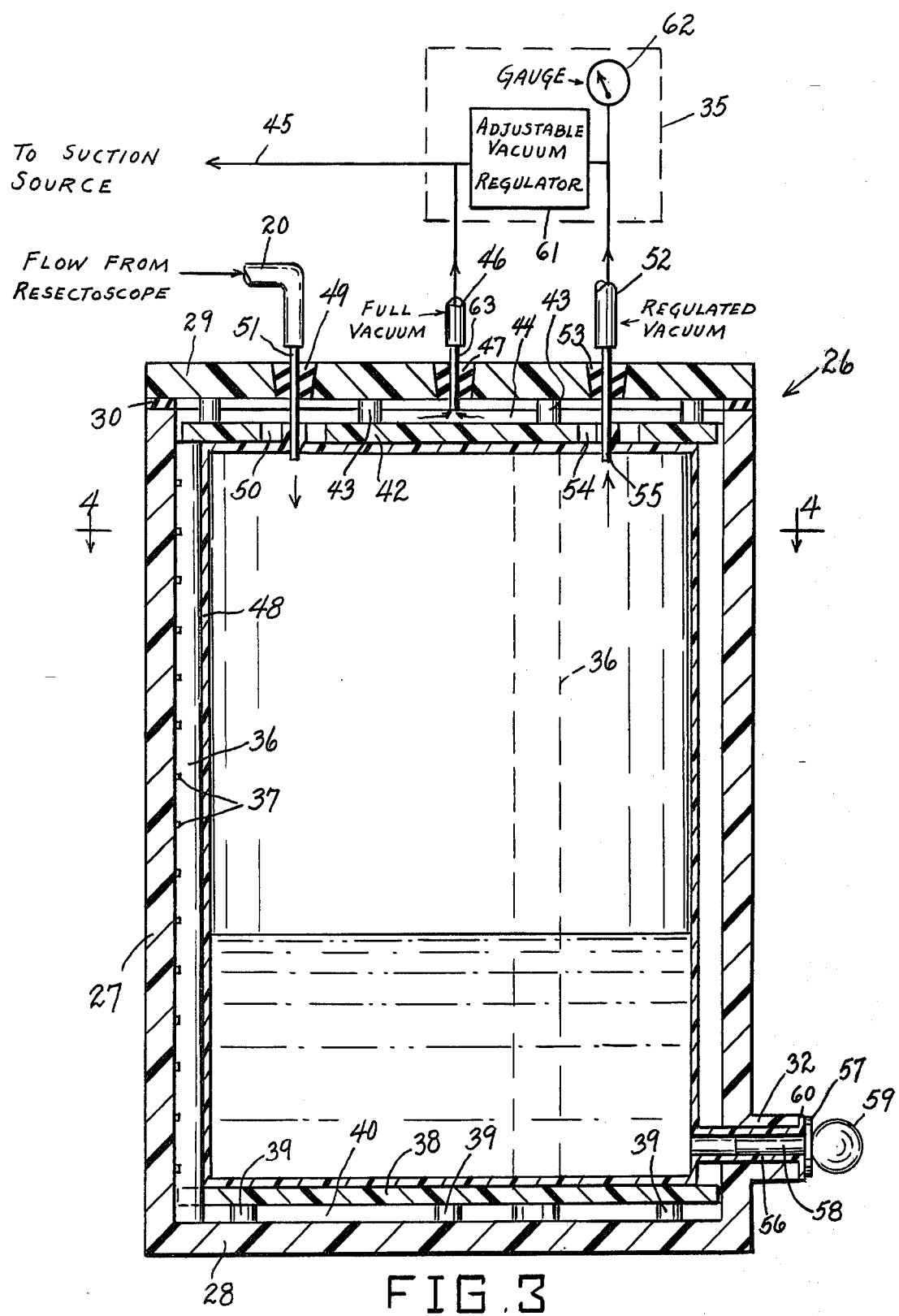

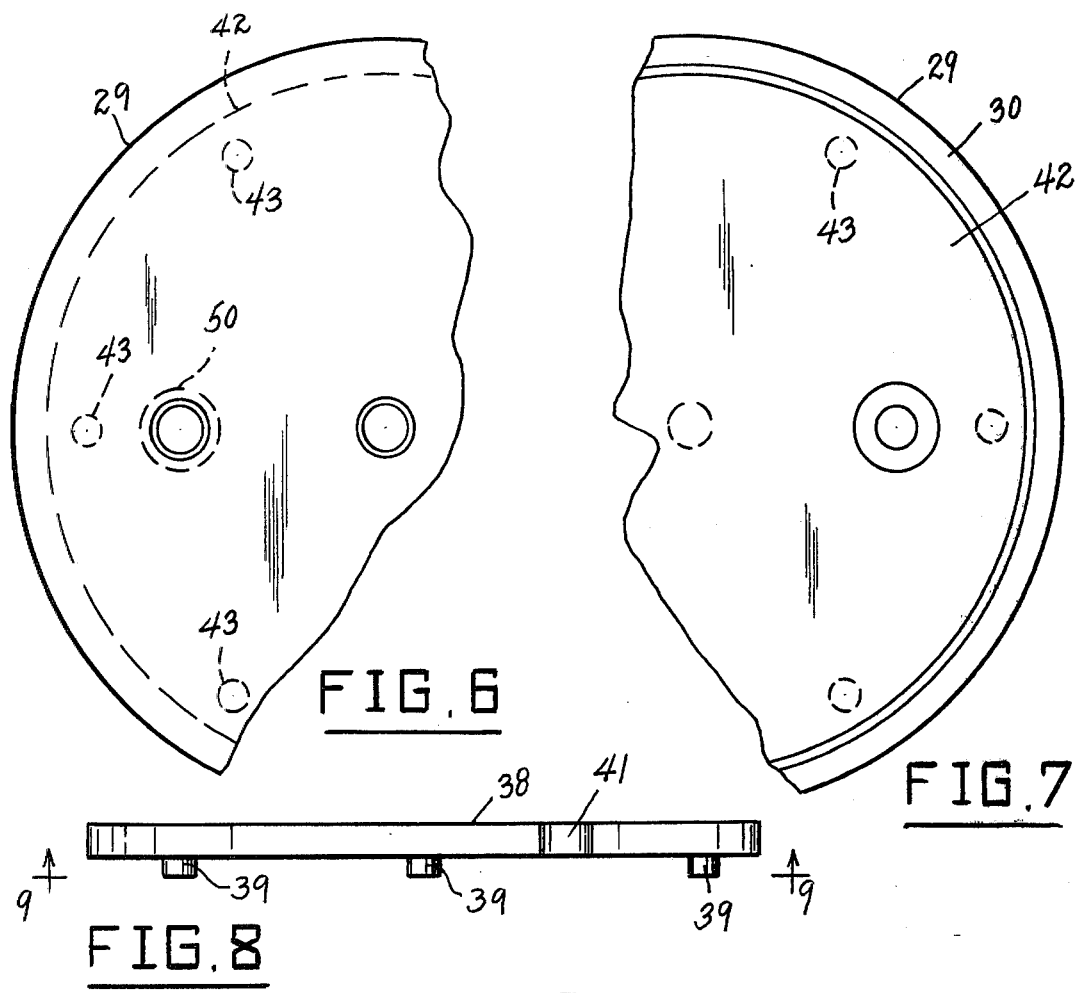
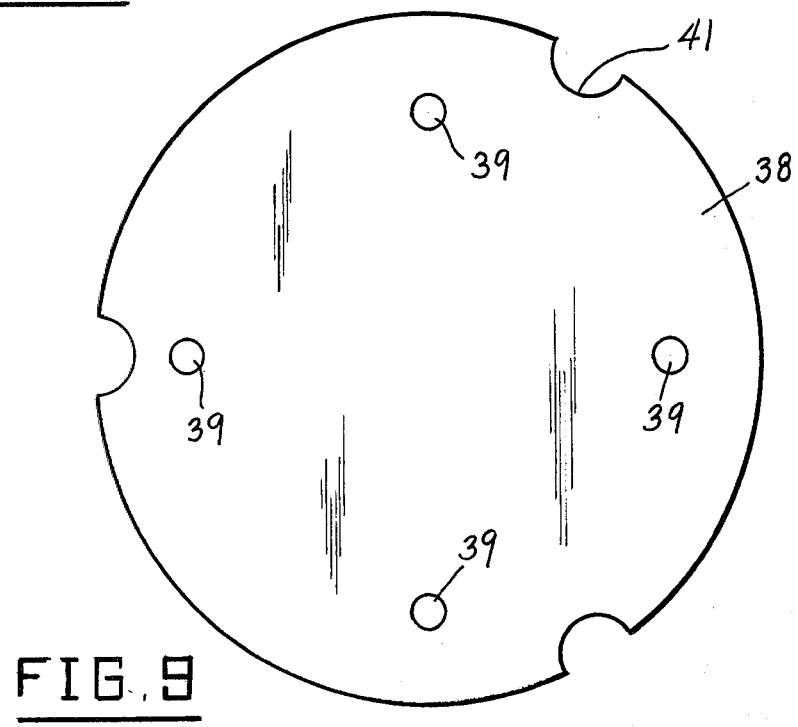

VACUUM UROLOGICAL SURGICAL IRRIGATING SOLUTION COLLECTING SYSTEM

FIELD OF THE INVENTION

This invention relates to surgical liquid collection systems, and more particularly to a vacuum urological surgical irrigation solution collecting system of the continuous flow type employed in connection with surgical procedures inside the urinary bladder, such as procedures performed with a resectoscope or similar surgical instrument.

BACKGROUND OF THE INVENTION

For many years surgical procedures inside the urinary bladder have been performed with an instrument called a "resectoscope", which is passed through the urethra (passageway for urine from the bladder to outside the body through the penis or vagina). This procedure has been performed with much greater frequency in the older male population due to the presence of a prostatic gland peculiar to the male. There are two different types of resectoscope apparatus, with distinctive differences:

(1) The non-continuous flow type (most widely used), usually referred to as the "regular" resectoscope. This regular resectoscope has a light source, a cutting electrode, a viewing lens system, and an irrigation system to fill and distend the bladder.

(2) The continuous flow type (C.F. resectoscope), which has all the systems of the regular resectoscope, with the addition of a vacuum port for the removal of surgical exudate fluids mixed with a continuing-flow irrigating liquid.

The usual continuous flow system employs a transfer pump for transfer of liquid, with a preset non-variable pressure, into an open container or bucket which requires dumping several times during a surgical procedure, with consequent delays of said procedure. The use of an open container is undesirable because it can cause cross-contamination of the room, the personnel, and the patient, and carries the risk of causing further cross-contamination between the janitorial dumping area and the urinary surgical area. The flow rate is invariable, being usually between 800 and 900 ml/min. The only control over the pressure is guesswork by the operator in limiting the orifice at the resectoscope discharge connection. By doing this it detracts from the potential full effectiveness of the continuous flow resectoscope and requires continual height adjustment of the gravity-feed infusion irrigation bottles. Furthermore, the C.F. resectoscope transfer pump is electric motor-driven, usually employing an extension cord. This adds to existing electrical hazards in the operating room. Also, airborne bacteria can be harbored in the housing of the apparatus and can be spread about the room by the action of the motor cooling fan. In addition, the transfer pump housing will be bathed in surgical fluid, grossly contaminated and used or shared by different patients, and ordinarily is not dismantled and cleaned between successive cases.

Variations of the previously used vacuum continuous flow systems have employed a number of receiving bottles to collect the flow, for example, five or six bottles (about 2000 ml each in volume) requiring only to be dumped or replaced two or three times during a procedure. Again, this tends to cause contamination associated with dumping, surgical delay while reestablishing reservoir space, and distraction of staff personnel from more critical duties. Over the years, the American Hospital Accreditation, several state regulatory agencies and infectious control groups have been making efforts to close or seal off the open floor drains in the urological surgical rooms. This has been met with much opposition because there has not existed a satisfactory collecting system. Some states have had these drains sealed, leaving the OR staff searching for a solution.

A preliminary search of the patented prior art revealed the following prior U.S. patents of interest:

| Erikson | 2,597,715 | Deaton et al | 3,848,628 |
|---|---|---|---|
| Folkman et al | 3,529,599 | Vaillancourt et al | 3,861,396 |
| Pannier et al | 3,680,560 | Ayres | 3,874,367 |
| Reynolds et al | 3,685,517 | Kaplan et al | 3,908,660 |
| Sorenson et al | 3,704,709 | De Wall | 3,946,735 |
| Pannier et al | 3,719,197 | Friend | 3,982,546 |
| Ikeda | 3,845,765 | | |

SUMMARY OF INVENTION

The present invention is therefore concerned with solving the many problems which have heretofore limited the optimum efficiency of the continuous flow resectoscope, and with adding newly advantageous features. For example, some of the problems previously experienced and which are dealt with by the present invention are as follows:

(1) The surgical procedure can be accomplished without unnecessary interruptions. This is important because:

a. Interruptions lengthen surgical time, anesthetic exposure time, and tend to increase the morbidity and mortality percentages due to the higher risk patient most often dealt with, as defined by the American Anesthesiologist Association.

b. With shorter surgical time the percentage rate for post-operative complications is proportionately lower.

c. With uninterrupted surgery, C.F. resectoscope principles remain constant and the patient will have less blood loss.

d. Highly trained nursing personnel can attend to more critical duties than dumping or changing containers, which will in turn give the patient better overall care.

e. The patient's cost is lower since the surgical room and anesthetic time are charged by the minute.

f. Shorter surgical procedure will allow better utilization of the hospital's surgical facility, the surgeon's time, the operating room staff, and the anesthesiologist's time.

(2) The total amount of fluid discharged during the entire procedure can be examined at any time or continually from the commencement to termination. This is important because:

a. Blood loss can constantly be estimated by viewing the discharged liquid.

b. It is easier, and with less likelihood of mistake, to keep track of liquid infused and liquid discharged, which could be critical if a vascular sinus were opened during surgery and liquid were to be siphoned into a vascular compartment, causing hemolysis and/or congestive failure. If this situation were not recognized the result could be fatal.

c. With the total amount of irrigation liquids and the total amount of surgical exudate in a single container, a sample can be drawn off, sent to a laboratory, and a hematocrit determination made (this gives a more exacting blood loss determination). This is of value only if all the liquids are in one container when the determining sample is taken.

(3) With the total amount of surgical discharged fluids in one closed container, it is less likely to contaminate the patient, the operating room, staff personnel, etc., and it makes terminal cleaning of the room easier, faster and more efficient in maintaining a sterile environment.

(4) The system of the present invention employs a closed sterile arrangement for each patient, in accordance with approved sterilizing methods used in hospitals today.

(5) The system of the present invention employs a fine-adjustment vacuum regulator and a vacuum bladder which assures a balanced urological surgical atmosphere within the urinary bladder. This is one of the most important aspects of the C.F. resectoscope assembly of the present invention. A second, much higher, vacuum is maintained outside of the vacuum bladder between the external surface thereof and the inside wall surfaces of the rigid surrounding container, including the top and bottom surfaces.

Accordingly, an object of the invention is to provide an improved resectoscope assembly system which overcomes the deficiencies and the shortcomings of the previously employed systems and apparatus employed for urinary bladder surgical procedures.

A further object of the invention is to provide an improved urological surgical irrigation solution collecting system of the continuous flow type which eliminates delays in surgical procedures by removing the necessity of frequently dumping or replacing liquid collection bottles or other containers, which minimizes cross-contamination, which avoids distraction of staff personnel from other critical duties, and which greatly reduces the surgical time involved in performing a urological surgical procedure.

A still further object of the invention is to provide an improved continuous flow resectoscope system which employs a liquid receiver of the type having a flexible disposable collecting receptacle supported in a rigid container, both under vacuum, and wherein an accurately controlled pressure gradient is maintained between the flexible inner receptacle and the rigid container, whereby to maintain the inner receptacle in a fully expanded condition, and wherein free circulation is assured in the space between the inner receptacle and the rigid outer container.

A still further object of the invention is to provide an improved surgical irrigating solution collecting vacuum chamber employing a flexible thin-walled disposable inner sack or receptacle within a rigid outer supporting container, with a space therebetween which is accurately maintained at a higher vacuum than that of the inner receptacle so as to hold the inner receptacle in an expanded condition, and wherein spacer means is provided all around the inner receptacle which defines said space but which allows free circulation therein, the chamber being usable with a conventional hospital suction line, allowing an associated surgical procedure to be conducted without interruptions, with minimum risk of blood loss, cross-contamination and anesthetic overexposure of a patient, with a saving in cost to the patient, and enabling easy monitoring of the irrigating liquid and surgical exudate from the associated surgical procedure.

A still further object of the invention is to provide an improved surgical irrigating solution collecting vacuum chamber having the advantages pointed out above, for use in a continuous flow resectoscope for performing surgical procedures inside the urinary bladder, the chamber having an inner disposable flexible sack or receptacle supported in an outer rigid container, the space around the inner sack being held at full vacuum from the hospital vacuum line and the inner sack or receptacle being held at an accurately controlled lesser vacuum, which can be finely adjusted as required, so as to provide desired expansion of the inner sack or receptacle at all stages of a surgical procedure, but being arranged to allow the collected surgical irrigation liquid and exudate to be examined all through the procedure and to permit a sample to be drawn off at any time for hematocrit determination or other study.

BRIEF DESCRIPTION OF THE DRAWINGS

Further objects and advantages of the invention will become apparent from the following description and claims, and from the accompanying drawings, wherein:

FIG. 1 is a diagrammatic view of a typical prior art continuous flow resectoscope and transfer pump system as employed for a surgical procedure inside the urinary bladder.

FIG. 2 is a side elevational view of an improved urological surgical irrigation solution and exudate vacuum collection chamber according to the present invention, adapted to be used in a continuous flow resectoscope system so as to overcome the disadvantages of the prior art systems.

FIG. 3 is an enlarged vertical cross-sectional view taken through the collection chamber of FIG. 2.

FIG. 6 is a fragmentary top plan view of the top cover member, taken substantially on the line 6—6 of FIG. 5.

FIG. 7 is a fragmentary bottom view of the top cover member, taken substantially on the line 7—7 of FIG. 5.

FIG. 8 is an enlarged side elevational view of the bottom spacer member employed in the collection chamber of FIG. 2.

FIG. 9 is a bottom view of the spacer member, taken substantially on the line 9—9 of FIG. 8.

DESCRIPTION OF A PREFERRED EMBODIMENT

Figure 4:
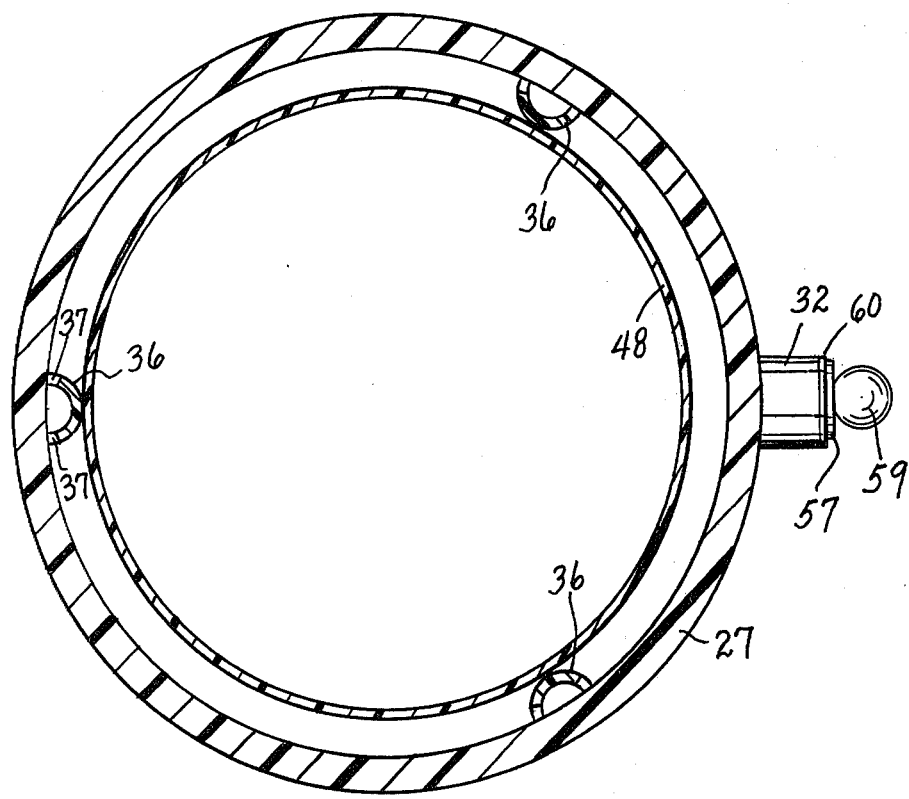
FIG. 4 is a horizontal cross-sectional view taken substantially on the line 4—4 of FIG. 3.
Figure 5:
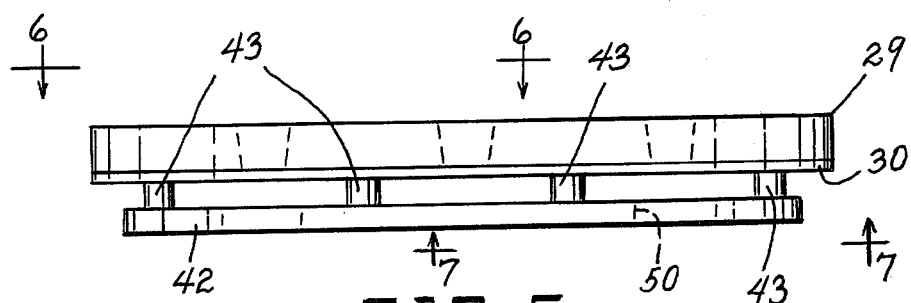
FIG. 5 is an enlarged side elevational view of the top cover member of the collection chamber of FIG. 2.

Referring to the drawings, FIG. 1 illustrates a typical prior art continuous flow resectoscope and transfer pump system employed for a surgical procedure inside a urinary bladder, shown diagrammatically at 11. In the system of FIG. 1, irrigating solution 12 is contained in suitably suspended bottles 13 and is conveyed via a conduit 14 and control valve 15 to a resectoscope 16. The resectoscope 16 includes a double wall catheter tube 17 insertable through the patient's urethra into the bladder 11, the catheter tube being provided at its inserted end with an inlet opening 18 and outlet apertures 18' to allow circulation of the irrigating liquid into the bladder and return thereof, with surgical exudates, through the catheter tube. The irrigating liquid and surgical exudates leave the resectoscope via an exit control valve and exit tube 20. The resectoscope includes a surgical cutting mechanism 21 and a lens system and eyepiece assembly 22. An electric motor-driven transfer pump 23 is employed to pump the irrigating liquid and exudates into a collection bucket 24 via a discharge tube 25.

As was pointed out above, the prior art system of FIG. 1 suffers from numerous disadvantages due to the use of the electric motor-driven pump 23 and the open receiving bucket or receptacle 24. As above mentioned, the use of the transfer pump 23 creates electrical hazards as well as contamination risks. Likewise, the use of an open receiving container or bucket causes delays since it requires frequent emptying and is also a source of serious contamination risk.

Other prior art systems employ receiving bottles, or the like, and vacuum compressor means or a vacuum source to induce suction in the discharge tube 20 to draw the irrigating liquid and surgical exudates into the receiving bottles. These other prior art systems are generally subject to the same disadvantages as the system shown in FIG. 1, as is the regular resectoscope procedure where surgery must be periodically and repeatedly interrupted to spill blood-reddened liquid from the bladder.

In accordance with the present invention, the irrigating liquid and surgical exudates from the resectoscope 16 are collected in a collection chamber assembly designated generally at 26 in FIG. 2. The collection chamber assembly 26 comprises a generally cylindrical vertical rigid outer supporting container 27 of suitable transparent material, such as transparent plastic material, having an integral bottom wall 28 and a removable circular top cover member 29 provided with an annular resilient deformable sealing gasket 30 sealingly engageable with the top rim of the cylindrical main container 27, as shown in FIG. 3. The main container 27 may be inscribed with a volumetric scale 31 calibrated in suitable volume units. Container 27 is integrally formed at its lower end portion with a drainage conduit 32.

The container 27 is supported on a wheeled platform 33 having rigidly secured thereto at one side edge an upstanding post member 34, to the top end of which is secured a vacuum control unit 35.

Rigidly secured inside container 27 and spaced uniformly around its interior surface are a plurality of substantially semicylindrical hollow spacer members 36 with their rounded portions facing inwardly, as shown in FIG. 4. The spacers 36 are provided at their opposite side edges with a plurality of uniformly vertically spaced pairs of diametrically opposite apertures 37,37 to insure free gas circulation through the spacers.

A generally circular bottom spacer member 38 is provided in the container 27, said spacer member 38 having a plurality of spaced depending supporting pins 39 engaging the container bottom wall 28 to support member 38 substantially parallel to bottom wall 28 and to define a circulation space 40 communicating with the spaces between the vertical spacers 36. Spacer member 38 has peripheral notches 41 conformably receiving the respective vertical spacers 36.

The top cover member 29 is provided with a generally circular spacer member 42 spaced therefrom parallel thereto by a plurality of spaced connecting pins 43, defining a circulation space 44 also communicating with the spaces between the vertical spacers 36.

A main vacuum conduit 45 is connected from a suction source, such as the hospital vacuum line, to the vacuum control unit 35. As shown in FIG. 3, conduit 45 is connected directly to space 44 via a conduit 46 and a nipple tube 63 passing sealingly through a resilient deformable plug 47 provided substantially centrally in top cover 29.

A disposable collection sack or bladder 48 of thin flexible transparent material, such as transparent plastic material, is disposed inside the rigid main supporting container 27. The flow conduit 20 from the resectoscope 16 is connected to the top of sack 48 through a resilient deformable plug 49 in top cover 29 and an aperture 50 in spacer disc 42, for example, by means of a suitable nipple tube 51, as shown in FIG. 3. A regulated vacuum supply conduit 52 connects the vacuum control unit 35 to the top of sack 48 through a resilient deformable plug 53 in cover member 29 and an aperture 54 in spacer disc 42, for example, by means of a suitable nipple tube 55.

The sack 48 is provided at its lower portion with an outlet conduit 56 passing through rigid conduit 32 and flanged at its outer end, as shown at 60, to engage over the rim of conduit 32, and adapted to be held sealingly thereagainst by the rigid flange 57 of a rigid removable sealing plug 58 provided with a spherical handle 59, as shown in FIG. 3.

Finely adjustable regulated vacuum control is provided between the full-vacuum line 45 and the regulated vacuum conduit 52 by a manually adjustable conventional vacuum regulator 61 connected therebetween, for example, of the type disclosed in U.S. Pat. No. 3,998,227 to Holbrook et al, issued Dec. 21, 1976. A conventional vacuum gauge 62 connected to line 52 indicates the degree of vacuum in the sack 48.

In operation, full vacuum is imposed on the space in the rigid container 27 around the sack 48, whereas carefully regulated reduced vacuum is imposed on the interior of the sack, thereby providing a pressure gradient to assure full inflation of the sack at all times during the surgical procedure. This gradient holds the sack 48 against the spacers 36, 38 and 42, with free circulation being assured around the sack to permit complete and rapid evacuation of the space between the sack 48 and the rigid container 27.

With the resectoscope inserted into the bladder 11 through the urethra, as in FIG. 1, the bladder 11 is then distended with gravity pressure irrigating fluid 12 via tubing 14 and valve 15. When this is achieved, the surgical field is observed by means of the eyepiece and lens system 22, and surgery is performed with the cutting electrode mechanism 21. The opening of the valve 19 allows the irrigating liquid and surgical exudates to be drawn into the sack 48, held inflated by the above-mentioned pressure gradient. A sample of the collected liquid may be drawn off for examination at any time during the procedure by temporarily releasing the vacuum applied to the interior of the sack 48 and removing the plug 58 to allow the desired sample to empty into a suitable receptacle.

The sack 48 may be discarded after a single use, or may be sterilized for reuse.

As above mentioned, the container assembly 26 is designed to maintain a vacuum around the outside of the sack or bladder 48. In order for the sack 48 to remain fully expanded with a vacuum inside, it is necessary to maintain a higher vacuum between the rigid container 27 and all the outside surfaces of the sack or bladder 48. The spacer elements 36, 38 and 42 cooperate with the vacuum regulator 61 to enable the required substantially constant pressure differential between the inside of the container 27 and the inside of the sack or bladder 48 to be maintained by positively defining the high-vacuum space between the container 27 and the sack 48.

It will be noted that the above-described connection of the collection chamber assembly 26 to the resectoscope 16, forming an improved system according to the present invention provides the various important advantages previously mentioned. Thus, the disadvantages accompanying the usage of an open collection bucket, an open floor drain with a drain trap in the operating room, or other collection or liquid disposal means as previously employed in the prior art, are completely avoided. For example, with the prior art practice, during surgery performed with the cutting mechanism 21 with a system such as that of FIG. 1, with the inevitable bleeding as surgery progresses, the visibility through the viewing system 22 becomes more limited proportionately with the amount of time and amount of bleeding. Soon the surgeon is unable to see anything but red-colored liquid and must stop surgery in order to remove the red liquid from the bladder 11 by emptying it into a catch tray, and frequently with much falling to the floor. The catch tray may have a hose which conveys the liquid to an open bucket, which will require intermittent dumping, and the floor may have an open drain with a conventional drain trap such as that in a shower floor. The bladder 11 is thereafter refilled and again emptied in the same way to flush out clots and continuing bleeding. Having accomplished this, surgery may continue, but these manouvers may need to be repeated many times before surgery is completed. By the time the surgical procedure is completed the floor may be covered with blood and water as a result of emptying the bucket several times. These undesirable conditions are avoided by the system of the present invention.

While a specific embodiment of an improved vacuum surgical irrigating solution collecting system has been disclosed in the foregoing description, it will be understood that various modifications within the scope of the invention may occur to those skilled in the art. Therefore, it is intended that adaptations and modifications should and are intended to be comprehended within the meaning and range of equivalents of the disclosed embodiments.

For example, while the system has been described with reference to the CF resectoscope, it will be understood that it can be used in conjunction with a regular resectoscope, and, indeed, with other systems involving flushing and drainage where sanitation is particularly important; in such other environments the invention will provide many of the same advantages noted above.

What is claimed is:

1. In a vacuum surgical irrigating solution-collecting apparatus, a drainage collecting assembly comprising a rigid outer supporting container having a top cover, spacer means within the container and top cover defining a continuous space adjacent the inside surfaces of the container and top cover, a flexible thin-walled disposable collecting receptacle in the rigid container engageable with said spacer means, a vacuum source for drawing vacuum at a first pressure, inlet conduit means communicatively connected to said collecting receptacle for admitting surgical irrigating solution, vacuum conduit means directly communicatively connecting said vacuum source to said continuous space to place said continuous space at substantially said first pressure, and finely adjustable vacuum-reducing means communicatively connecting said vacuum source to said collecting receptacle and placing the interior of said collecting receptacle at a second pressure higher than said first pressure to maintain said collecting receptacle in an inflated condition, said second pressure being sufficiently high as to not collapse a patient's bladder.

2. The drainage collecting assembly of claim 1, and wherein said top cover is removably mounted on said rigid supporting container.

3. The drainage collecting assembly of claim 2, and sealing gasket means between said top cover and said supporting container.

4. The drainage collecting assembly of claim 1, and wherein said rigid container has a drain conduit at its lower portion and said collecting receptacle is provided with a drain tube exiting from the lower end of said collecting receptacle and extending through said drain conduit; said rigid container being provided with wheel means.

5. In a vacuum surgical irrigating solution-collecting apparatus, a drainage collecting assembly comprising a rigid outer supporting container having a top cover, spacer means on the container and top cover defining a continuous space adjacent the inside surfaces of the container and top cover, a flexible thin-walled disposable collecting receptacle in the rigid container engageable with said spacer means, a vacuum source, inlet conduit means communicatively connected to said collecting receptacle for admitting surgical irrigating solution, vacuum conduit means directly communicatively connecting said vacuum source to said continuous space to provide a first pressure in said space, and vacuum-reducing means communicatively connecting said vacuum source to said collecting repectacle and placing the interior of said collecting receptacle at a second pressure higher than the first pressure and sufficient to maintain said collecting receptacle in an inflated condition, and wherein said spacer means includes a plurality of spaced hollow elongated apertured upstanding members secured to and projecting inwardly from the inside surface of said rigid container.

6. The drainage collecting assembly of claim 1, and wherein said spacer means includes a platelike member disposed below said collecting receptacle and having a plurality of spaced depending abutment elements engaging the bottom wall of the rigid container.

7. The drainage collecting assembly of claim 1, and wherein said spacer means includes a platelike member disposed above said collecting receptacle, and a plurality of spaced pin elements supportingly connecting said platelike member to said top cover.

8. The drainage collecting assembly of claim 1, and wherein said spacer means includes a plurality of spaced, elongated, upstanding members secured to and projecting inwardly from the inside surface of said rigid container, said upstanding spacer members having openings therethrough to assure free gas circulation, and a bottom platelike member disposed below said collecting receptacle and having a plurality of spaced depending abutment elements engaging the bottom wall of the rigid container, whereby to define a bottom circulation space communicating with the spaces between the upstanding members.

9. The drainage collecting assembly of claim 8, and wherein said platelike bottom member has peripheral notches conformably receiving said upstanding members.

10. The drainage collecting assembly of claim 8, and wherein said upstanding members are hollow and are formed with a plurality of vertically spaced apertures.

11. The drainage collecting assembly of claim 8, and wherein said spacer means includes a top platelike member disposed above said collecting receptacle and spaced pin elements supportingly connecting said top platelike member to said top cover and defining a top circulation space communicating with the spaces between said upstanding members.

12. The drainage collecting assembly of claim 1, and wherein said outer supporting container and said collecting receptacle are made of transparent material and said outer supporting container is inscribed with a volumetric scale.

13. The drainage collecting assembly of claim 1, and wherein said vacuum-reducing means is adjustable for varying the degree of reduced vacuum in the interior of said collecting receptacle.

14. The drainage collecting receptacle of claim 1, and wherein said vacuum-reducing means comprises an adjustable vacuum regulator connected between said vacuum source and said collecting receptacle.

15. In a vacuum surgical irrigating solution-collecting device of the continuous flow type, a drainage collecting assembly comprising a rigid outer supporting container, a flexible thin-walled collecting receptacle disposed inside the supporting container, spacer means within the supporting container defining a space between substantially all of the exterior surface of the collecting receptacle and the outer supporting container, a vacuum source for drawing vacuum at a first pressure, inlet conduit means communicatively connected to said collecting receptacle for admitting surgical irrigating solution, conduit means directly connecting said vacuum source to said space to provide substantially said first pressure in said space, and finely adjustable control means to place the interior of said collecting receptacle at a second pressure higher than said first pressure to maintain said collecting receptacle in an inflated condition.

16. The drainage collecting assembly of claim 15, and wherein said means to place the interior of the collecting receptacle at a degree of vacuum lower than that in said space comprises a vacuum regulator connected between said vacuum source and said flexible collecting receptacle.

* * * * *